US007209796B2

(12) United States Patent
McKinney et al.

(10) Patent No.: US 7,209,796 B2
(45) Date of Patent: Apr. 24, 2007

(54) AUSCULTATORY TRAINING SYSTEM (75) Inventors: Walter G. McKinney, Morgantown, WV (US); Jeff S. Reynolds, Morgantown, WV (US); Kimberly A. Friend, Leesburg, VA (US); William T. Goldsmith, Masontown, WV (US); David G. Frazer, Fairmont, WV (US)

(73) Assignee: The United States of America as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 785 days.

(21) Appl. No.: 10/135,964

(22) Filed: Apr. 29, 2002

(65) Prior Publication Data

US 2002/0183874 A1 Dec. 5, 2002

Related U.S. Application Data (60) Provisional application No. 60/287,941, filed on Apr. 30, 2001.

(51) Int. Cl.
*G06F 17/00* (2006.01)
*A61B 7/04* (2006.01)
*H04B 15/00* (2006.01)
*G09B 23/28* (2006.01)

(52) U.S. Cl. .................. 700/94; 381/67; 381/71.7; 381/94.2; 434/266

(58) Field of Classification Search ............ 700/94; 434/266; 600/528, 586; 381/67, 71.1, 71.6, 381/71.7, 94.1, 94.2
See application file for complete search history.

(56) References Cited

U.S. PATENT DOCUMENTS 3,849,909 A 11/1974 Ravin (Continued)

FOREIGN PATENT DOCUMENTS

JP 59011098 A2 1/1984

(Continued)

OTHER PUBLICATIONS

Goldsmith, W.T., et al., "Frequency Time and Energy Analysis of Cough Sounds," ECTB, HELD, and CIB, DRDRS, National Institute for Occupational Safety and Health, and Pulmonary and Critical Care Medicine, WVU School of Medicine, Morgantown, WV 26505. Presented at International Lung Sounds Conference Oct. 1998, in Boston, MA and published in proceedings.

(Continued)

*Primary Examiner*—Sinh Tran
*Assistant Examiner*—Daniel R. Sellers
(74) *Attorney, Agent, or Firm*—Klarquist Sparkman, LLP (57) ABSTRACT

According to a disclosed embodiment, an auscultatory training apparatus includes a database of pre-recorded physiological sounds stored on a computer for playing on a playback system. A user-friendly, graphical user interface software program is stored on the computer for use with a conventional computer mouse. The program allows a user to select one of the pre-recorded sounds for playback. In addition, the program is operable to generate an inverse model of the playback system in the form of a digital filter. If employed by the user, the inverse model processes the selected sound to cancel the distortions of the playback system so that the sound is accurately reproduced in the playback system. The program also permits the extraction of a specific sound component from a pre-recorded sound so that only the extracted sound component is audible during playback.

9 Claims, 5 Drawing Sheets

U.S. PATENT DOCUMENTS

| | | | |
|---|---|---|---|
| 4,254,302 | A | 3/1981 | Walshe |
| 4,463,764 | A | 8/1984 | Anderson et al. |
| 4,991,581 | A * | 2/1991 | Andries .................. 600/528 |
| 5,226,000 | A | 7/1993 | Moses et al. |
| 5,337,752 | A * | 8/1994 | Reeves .................. 600/513 |
| 5,481,614 | A | 1/1996 | Johnston |
| 5,492,129 | A * | 2/1996 | Greenberger ............ 600/528 |
| 5,499,302 | A * | 3/1996 | Nagami et al. ........... 381/71.4 |
| 5,520,191 | A * | 5/1996 | Karlsson et al. .......... 600/515 |
| 5,539,831 | A * | 7/1996 | Harley .................. 381/67 |
| 5,745,396 | A * | 4/1998 | Shanbhag ................ 708/322 |
| 5,832,093 | A | 11/1998 | Bernstein et al. |
| 5,868,579 | A | 2/1999 | Lampotang et al. |
| 5,909,495 | A * | 6/1999 | Andrea .................. 381/67 |
| 6,005,951 | A | 12/1999 | Grasfield et al. |
| 6,026,170 | A | 2/2000 | Dieken et al. |
| 6,075,475 | A | 6/2000 | Ellis et al. |
| 6,134,331 | A | 10/2000 | Bækgaard |
| 6,139,505 | A | 10/2000 | Murphy |
| 6,178,250 | B1 * | 1/2001 | Brungart et al. .......... 381/337 |
| 6,220,866 | B1 * | 4/2001 | Amend et al. ............ 434/266 |
| 6,436,057 | B1 | 8/2002 | Goldsmith et al. |

FOREIGN PATENT DOCUMENTS

| | | |
|---|---|---|
| JP | 1259838 A2 | 10/1989 |
| JP | 7046069 A2 | 2/1995 |
| WO | WO9834542 A2 | 8/1998 |

OTHER PUBLICATIONS

Frazer, D.G., et al., "Analysis of Cough Sounds As An Index of Lung Disease," PPRB, HELD and CIB, DRDS, National Institute for Occupational Safety and Health, and Pulmonary and Critical Care Medicine, WVU School of Medicine, Morgantown, WV 26505. Presented at the American Thoracic Society Meeting, Mar. 1998, and published in proceedings.

Friend, K.A., "Wavelet Analysis and Morphology for the Detection of Wheeze in Cough Sounds," Engineering and Control Technology Branch, Health Effects Laboratory Division, National Institute for Occupational Safety and Health, Morgantown, WV. Presented at the Biosignal Interpretation Workshop, Apr. 1999 in Chicago and published in proceedings.

Goldsmith, W.T., "A System for Recording High Fidelity Cough Sound Measurements," Engineering and Control Technology Branch, National Institute for Occupational Safety and Health, Morgantown, WV. Presented at the Biosignal Interpretation Workshop, Apr. 1999 in Chicago and published in proceedings.

Thorpe, C.W., et al., "Towards a Quantitative Description of Asthmatic Cough Sounds," Eur. Respir. J., No. 5, pp. 685-692 (1992).

Debreczeni, L.A., et al., "Spectral Analysis of Cough Sounds Recorded With and Without a Nose Clip", Bull. Eur. Physiopathol. Respir., No. 10, pp. 57s-61s.

Oppenheim, A. V., et al. "The Speech Model," In: Discrete-Time Signal Processing, Prentice Hall, Chapter 12, pp. 816-825.

Debreczeni, L.A., et al., "Spectra of the Voluntary First Cough Sounds," Acta Physiological Hungarica vol. 75, (2), pp. 117-131 (1990).

Yanagihara, N., et al., "The Physical Parameters of Cough: The Larynx in a Normal Single Cough," Acta Oto-laryngol., 61: 495-510 (1965).

Piirilä, P., et al., "Differences in Acoustic and Dynamic Characteristics of Spontaneous Cough in Pulmonary Diseases," Chest, 95:46-53 (1989).

Leith, D.E., et al.,"Cough," In: The Handbook of Physiology, the Respiratory System III, edited by A. Fishman, P.T. Macklem and J. Mead, Bethesda, MD, Chapter 20, pp. 315-336 (1987).

Toop, L.J., et al., "Cough Sound Analysis: A New Tool for the Diagnosis of Asthma?," Family Pract., vol. 6, No. 2, pp. 83-85 (1989).

Toop, L.J., et al., "A Portable System for the Spectral Analysis of Cough Sounds in Asthma", J. of Asthma, 27(6): 393-397 (1990).

Reynolds, J.S., et al., "A System for Reconstruction of Cough Sounds and Cough Sound Components." Presented at the International Lung Sounds Conference, Oct. 1999, and published in proceedings.

McKinney, W.G., et al., "A LabVIEW Based Respiratory Sounds Reconstuction Tool," Proceedings of the 46th ISA International Instrumentation Symposium, ISA vol. 397, pp. 327-224 (2000). Presented at the 46th ISA International Instrumentation Symposium, May 2000.

Goldsmith, W.T., et al., "An Improved System for Measuring Breath and Cough Sounds." Presented at the International Lung Sounds Conference, Oct. 1999 and published in proceedings.

Friend, K.A., et al., "Acoustic Tube Reconstruction for the Characterization of Cough Sounds," Engineering and Control Technology Branch, Health Effects Laboratory Division, National Institute for Occupational Safety and Health, Morgantown, WV. Presented at the Biomedical Engineering Society Meeting, Oct. 1999 and published in proceedings.

Friend, K.A., et al., "Wheeze Duration in Cough Sounds for Disease Characterization." Presented at the International Lung Sounds Conference, Oct. 1999 and published in proceedings.

Goldsmith, W.T., et al., "Simultaneous Breath Sound and Flow Measurements During Cough." Presented at the International Lung Sounds Conference, Sep. 2000 and published in proceedings.

Goldsmith, W.T., et al., "Mouth Flow Estimation During Cough Sound Measurements." Presented at the Southern Biomedical Engineering Conference, Apr. 2000 and published in proceedings.

Korpas, J., et al., "The Origin of Cough Sounds," Bull. Evr. Physiopathol. Respir., 47s-50s (1987).

Keleman, S.A., et al., "Information Obtained from Tussigrams and the Possibilities of Their Application in Medical Practice" (1987).

* cited by examiner

AUSCULTATORY TRAINING SYSTEM

PRIORITY CLAIM

This application claims priority to U.S. Provisional Application No. 60/287,941, filed on Apr. 30, 2001.

FIELD

The present invention relates to reconstructing pre-recorded sounds, and in particular, to reconstructing pre-recorded respiratory sounds for training health care workers in auscultation.

BACKGROUND

Since the invention of the stethoscope, physicians and other health care workers have used lung acoustics to assist in the diagnosis and analysis of the health ills and abnormalities of patients. Typically, less experienced medical personnel gain practical experience in the art of auscultation by listening to the heart and lung sounds of live patients.

Of course, patients are not always available to assist in the teaching process. Consequently, teaching apparatuses have been developed wherein recordings of actual patient respiratory sounds are used to train medical personnel in auscultation. However, current teaching tools which utilize previously recorded sounds suffer from the disadvantage that playback environments cause considerable distortion in the sounds that they reproduce. To those using such tools, the reproduced respiratory sounds do not "sound" as if they are being generated by a live patient. Moreover, the distortions may make it difficult for the listener to hear and/or interpret the subtleties of a recorded respiratory maneuver.

In addition, the diagnosis of respiratory problems often involves the identification of a specific component of a respiratory maneuver. As such, it would be desirable if specific sound components could be isolated from recorded respiratory maneuvers so that only those components are audible during playback. However, this cannot be accomplished using current state-of-the-art teaching apparatuses.

Thus, there exists a need for a new and improved system for training health care workers in auscultation.

SUMMARY

In view of the foregoing disadvantages inherent in conventional training apparatuses, the present invention provides an auscultatory training system capable of producing physiological sounds, such as respiratory sounds, as they were originally recorded. The present invention also provides an auscultatory training system operable to permit the selection of a specific sound component of a recorded physiological sound so that only that sound component is audible during playback.

According to one embodiment, an auscultatory training apparatus includes a computer and a playback system. The computer has memory means for digitally storing a database of pre-recorded, physiological sounds for playing on the playback system, means for selecting one of the pre-recorded sounds for playback, and means for generating an input digital signal of a sound selected for playback. A digital to analog converter converts the digital signal into an input analog signal. An analog to digital converter receives an analog output signal from the playback system and converts the output signal to a digital signal. A selectively operable reconstruction means reconstructs the input digital signal so as to cancel the distortions of the playback system for accurate audible reconstruction of the sound in the playback system. The reconstruction means may comprise, for example, an inverse model of the playback system in the form of a digital infinite impulse response filter.

The playback system includes an amplifier for receiving and amplifying the input analog signal from the digital to analog converter. An output speaker is connected to the amplifier for converting the analog signal received from the amplifier into an audible reconstruction of the selected sound. An elongate tubular member is positioned adjacent the speaker so that sound from the speaker travels through the tubular member. The end of the tubular member opposite the speaker is open. A listening mechanism, such as a stethoscope having an input end disposed inside the tubular member, enables a user to listen to the reconstructed sound. A microphone is mounted on the tubular member and electrically connected to the analog to digital converter of the computer. The microphone converts the audible sound into an output analog signal and transmits the output signal to the analog to digital converter.

According to another embodiment, an auscultatory training apparatus includes a playback system and a computer. A database of pre-recorded, human generated respiratory sounds for playing on the playback system are stored on the computer. In addition, a display mechanism, such as a computer monitor, and a multi-functional software program are provided to facilitate user interface with the training apparatus. In a disclosed embodiment, the program is a user-friendly, graphical user interface program that can be used in connection with a conventional computer mouse.

The program allows a user to select one of the pre-recorded sounds for playback. In addition, the program is operable to generate an inverse model of the playback system. The inverse model in one form is a digital infinite impulse response filter. If employed by the user, the inverse model processes the selected sound to cancel the distortions of the playback system so that the sound is accurately reproduced in the playback system. A time signal of the originally recorded sound along with a time signal of the sound reproduced in the playback system may be displayed on the monitor.

In addition, a spectrogram of the sound signal may be displayed on the monitor. In a disclosed embodiment, the spectrogram includes a horizontal time axis and a vertical frequency axis. Energy distribution of the sound signal is represented by a color scale. A portion of the spectrogram corresponding to a specific component of the sound may be selected for playback. This may be accomplished, for example, by freehand drawing a line around the portion corresponding to the specific sound component with the mouse so as to define an enclosed portion of the spectrogram. A digital filter, such as a second order Butterworth filter, may be employed to filter the enclosed portion from the unwanted portion of the spectrogram so that only the selected sound component is audible during playback.

A method for reconstructing a pre-recorded respiratory sound in a playback system for training health care workers in auscultation according to one embodiment comprises generating an inverse model of the playback system in the form of a digital infinite impulse response filter. A sound may be selected from a database of pre-recorded, digitally stored, human generated respiratory sounds. Once a sound is selected, a digital signal of the sound is generated and reconstructed with the digital filter so as to cancel the distortions of the playback system. The reconstructed signal of the selected sound is converted into an analog signal which is then converted into an audible reconstruction of the selected sound in the playback system to enable a user to listen to the selected sound.

According to another method for reconstructing a pre-recorded respiratory sound in a playback system for training health care workers in auscultation, an inverse model of the playback system is generated in the form of a digital filter. A sound may be selected from a database of pre-recorded, digitally stored, human generated respiratory sounds and then a specific component of that sound is selected for playback. A digital signal corresponding to the selected sound component is generated and a digital filter processes the signal to cancel the distortions of the playback system. The signal is converted into an analog signal which is then converted into an audible reconstruction of the selected component of the sound in the playback system to enable a user to listen to the selected sound component.

In a method for reconstructing a digital signal of a physiological sound, a spectrogram showing the time, frequency and energy distribution of the signal is generated. In one form, the spectrogram includes a horizontal time axis, a vertical frequency axis and energy distribution represented by a color scale. A portion of the spectrogram corresponding to a specific component of the sound is filtered from the remaining portion of the spectrogram. The filtered portion of the spectrogram is reproduced as an audible sound in a playback system.

The foregoing and other objects, features, and advantages of the invention will become more apparent from the following detailed description of several embodiments, which proceed with reference to the accompanying figures.

DETAILED DESCRIPTION

The training system as shown and described herein includes the use of software stored on a computer-readable medium and executed on a general-purpose computer. It should be understood, however, that the invention is not limited to any specific computer language, program or computer.

Computer readable media can be any available media that can be accessed by the computer. By way of example, and not limitation, computer readable media may comprise computer storage media and communication media.

Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by the computer.

Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

Figure 1:
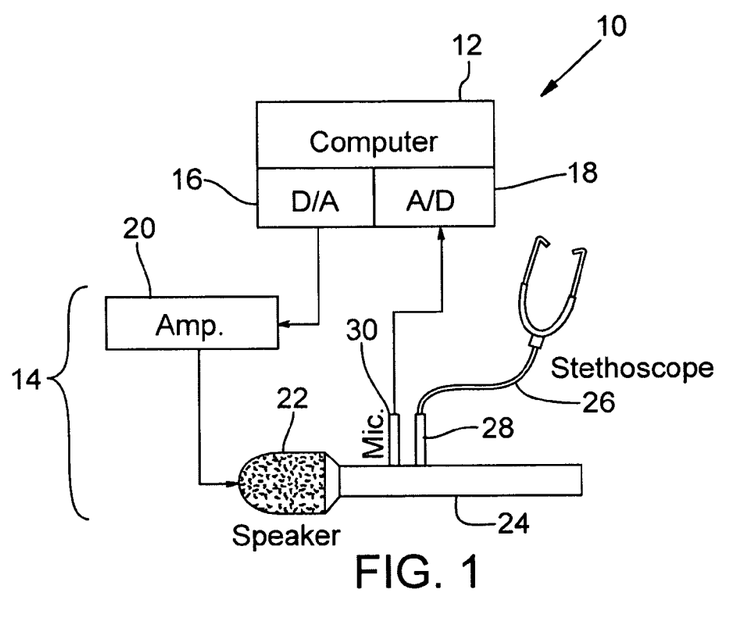
FIG. 1 is a diagram of an auscultatory training system according to one embodiment.

Referring then to FIG. 1, there is shown an apparatus 10 for reconstructing pre-recorded physiological sounds. The apparatus 10 includes a general purpose computer 12 and a playback system 14. A database of pre-recorded, physiological sounds are digitally stored on the computer 12. As described in greater detail below, the sounds may be selected for playback using software installed on the computer 12. Some examples of physiological sounds that can be stored on the computer for playback include, without limitation, respiratory sounds; cardiological sounds; intestinal sounds, such as bowel sounds; fetal heart sounds; or sounds made by a patient upon insertion of a nasogastric tube. Other non-human generated sounds, such as animal-related sounds, may be stored on the computer for playback.

The computer 12 in the form shown includes a digital to analog converter 16 and an analog to digital converter 18. The illustrated playback system 14 includes an amplifier 20 connected to the digital to analog converter 16. The amplifier 20 is connected to a speaker 22. An elongate tubular member 24 is positioned proximate the speaker 22 so that sound from the speaker travels through the tubular member. A listening mechanism, such as a stethoscope 26 having an input end inserted into an input port 28 of the tubular member 24, enables a user to listen to a sound reproduced in the playback system. Other forms of listening mechanisms also may be used. For example, an electronic stethoscope or headphones also may be used.

A microphone 30 is mounted tangentially on the outside of the tubular member 24 and connected to the analog to digital converter 18 of the computer 12. The microphone 30 desirably is mounted proximate to the input port 28 for the stethoscope 26 to enable the microphone and the stethoscope to obtain approximately the same sound pressure wave.

As can be seen in FIG. 1, a sound stored on the computer 12 and selected for playback is converted into an analog signal by the digital to analog converter 16 for input into the amplifier 20, which receives and amplifies the signal. The speaker 22 receives the signal from the amplifier and converts it into an audible sound. The microphone 30 converts the sound into an output analog signal which is transmitted to the analog to digital converter 18 of the computer.

Apparatus 10 can be modified for use as a recording system for recording respiratory sounds by replacing the speaker 22 with a mouthpiece. Sounds generated by a subject are transmitted to the digital to analog converter 18 were they are digitized and stored on the computer 12 as a database of pre-recorded sound files. Of course, when used as a recording system, an amplifier, a digital to analog converter or a stethoscope is not required.

In a working embodiment of apparatus 10, a model PCI-4451 National Instruments Dynamic Signal Acquisition and Generation (NI DAQ) card installed on a computer functions as both digital to analog converter 16 and analog to digital converter 18. The playback system 14 includes a Yamaha model RX-596 amplifier and an Atlas Sound model PD-5VH speaker. Tubular member 24 is a metal tube having a diameter of about 1 inch and a length of about eight inches. A 1 inch diameter metal tube was selected to match the upper air waves from the mouth of a subject when apparatus 10 is used as a recording system as explained in the preceding paragraph. However, other size tubes also may be used. A ¼ inch, Bruel & Kjaer model 4136 microphone is mounted on the metal tube approximately 1.5 inches from the input port 28 of the stethoscope 26.

Since the output of the playback system 14 can be determined from any known input, acoustic reconstruction techniques can be used to predict how the input to the amplifier 20 should be modified to cancel the distortions of the playback system for accurate audible reconstruction of pre-recorded sounds in the playback system.

According to one approach, an inverse model of the playback system is estimated in the form of a digital infinite impulse response (IIR) filter. A sound signal selected for playback is reconstructed by the IIR filter so that the sound is reproduced in the playback system as it was originally recorded. The IIR filter in one example is a 100th order digital filter, as represented by the following equation:

$$1/H(z) = \frac{1 + a_1 z^{-1} + a_2 z^{-2} + \ldots a_{100} z^{-100}}{b_0 + b_1 z^{-1} + b_2 z^{-2} + \ldots b_{100} z^{-100}}$$

A 100th order filter has been found to provide an accurate model of the playback system 14 with an acceptable computer processing time, although higher or lower order filters also may be used. The coefficients for the inverse filter may be solved by a batch least squares method, as is known in the art. Other types of filter structures, such as, neural networks or higher order statistics, can be used in lieu of the IIR filter.

Figure 2A:
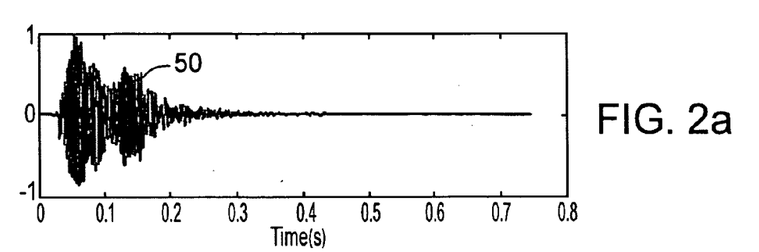
FIG. 2a shows a time signal of a previously recorded respiratory sound.
Figure 2B:
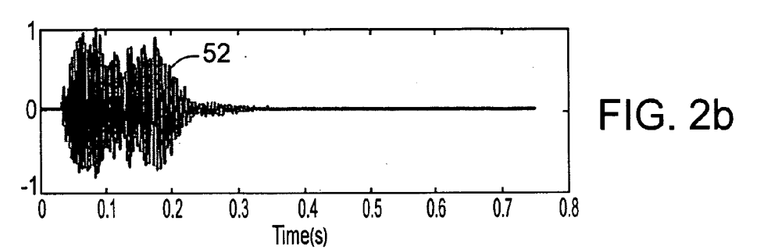
FIG. 2b shows a time signal of the previously recorded sound of FIG. 2a replayed without digital reconstruction.
Figure 2C:
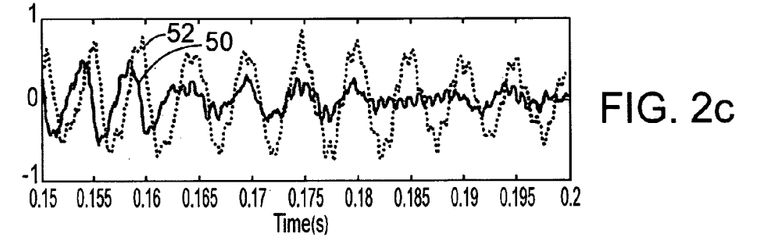
FIG. 2c shows an enlarged portion of the time signals of FIG. 2a and FIG. 2b.
Figure 2D:
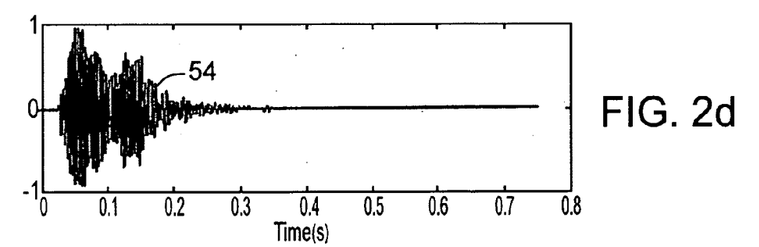
FIG. 2d shows a time signal of the previously recorded sound of FIG. 2a replayed with digital reconstruction.
Figure 2E:
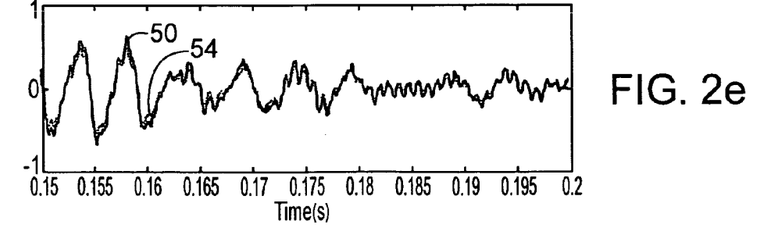
FIG. 2e shows an enlarged portion of the time signals of FIGS. 2a and 2d.

FIGS. 2a–2e illustrate the improvement in sound fidelity that can be achieved by reconstructing a sound signal with the IIR filter. FIG. 2a shows a time signal 50 of a sound as it was originally recorded. FIG. 2b shows a time signal 52 of the same sound reproduced in the playback system 14 without having been reconstructed by the IIR filter. Comparison of the two signals in FIG. 2c illustrates the distortions caused by the playback system. In contrast, FIG. 2d shows a time signal 54 of the sound reproduced in the playback system with acoustical reconstruction. As shown in FIG. 2e, reconstructed time signal 54 is a much more accurate reproduction of signal 50 than non-reconstructed time signal 52 (FIG. 2c).

Figure 3:
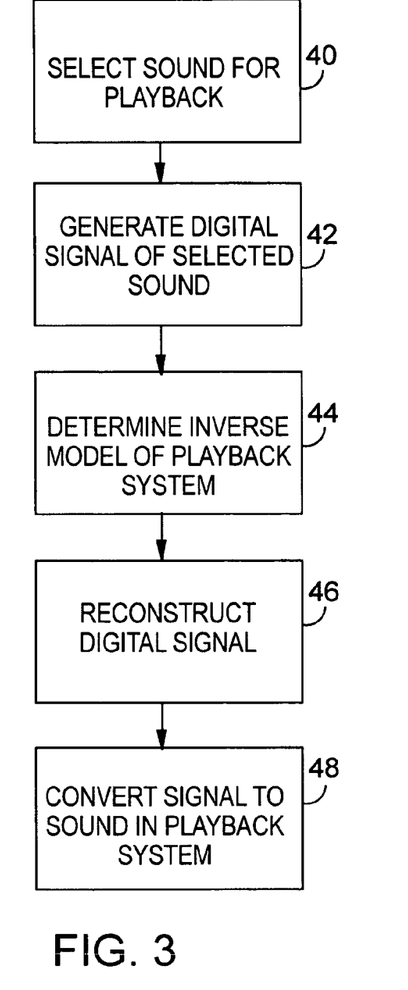
FIG. 3 is a flowchart showing a method for playing a pre-recorded respiratory sound.

Referring to FIG. 3, there is shown a flowchart for a method for playing a respiratory sound in the playback system 14. First, as shown in process block 40, a respiratory sound is selected for playback from the database of pre-recorded sounds. In process block 42, the computer generates a digital signal of the selected sound.

In process block 44, an inverse model of the playback system 14 in the form of an IIR filter is generated. As mentioned above, the inverse model may be determined from any known input and its corresponding output. In the present example, the selected sound is reproduced to obtain an output from the playback system for use in generating the model of the playback system. Once generated, the inverse model/digital filter may be saved in the memory of the computer for later use.

In process block 46, the signal is reconstructed by the digital filter to cancel the distortions of the playback system. Finally, the signal is converted to an audible sound in the playback system, as shown in process block 48.

The method described above (process blocks 40–48 of FIG. 3) may be repeated to reconstruct additional sounds in the database. In addition, it is possible to create a collection of digitally stored models, with each corresponding to one of the pre-recorded sounds in the database. Thus, once a model is generated using a particular sound file, that model can be recalled for future use in replaying the sound.

In an alternative approach, a previously saved model corresponding to one sound may be used to reconstruct another sound, although this may be less desirable because the latter sound may contain frequencies not present in the sound used to generate the original model. These new frequencies may excite a portion of the playback system which is not represented by the model, and thereby adversely effect the accuracy with which the signal is reconstructed.

In yet another approach, a white noise file (i.e., a sound file containing all frequencies) may be used to generate a generic model for reconstructing all sound files in the database. After the first time such a generic model is generated, it may be saved for future use in reconstructing any sound file in the database.

In addition, a sound signal may be saved in its reconstructed form, in which case further processing of the signal by the inverse model is not required if and when it is selected for playback at a later time. Moreover, apparatus 10 can be used to create a database of pre-reconstructed sound files for use with apparatuses having like playback systems. Thus, if an apparatus has such a database, it would not be necessary to generate inverse models or process sound signals with inverse models for accurate reproduction in a playback system. Also, the playback system 14 would not require a microphone 28 or digital to analog converter 18 to provide output signals to the computer for the generating inverse models. This embodiment, however, may be less desirable because day-to-day atmospheric factors that effect the output of the playback system (e.g., atmospheric temperature or pressure) can not be accounted for in an earlier created model.

A working embodiment of apparatus 10 includes a user-friendly, graphical user interface software program stored on the computer 12. A computer monitor or other display means is used to display the various screens or windows of the program. A conventional computer mouse may be used to facilitate user interface with the program, as is well known in the art.

Figure 5:
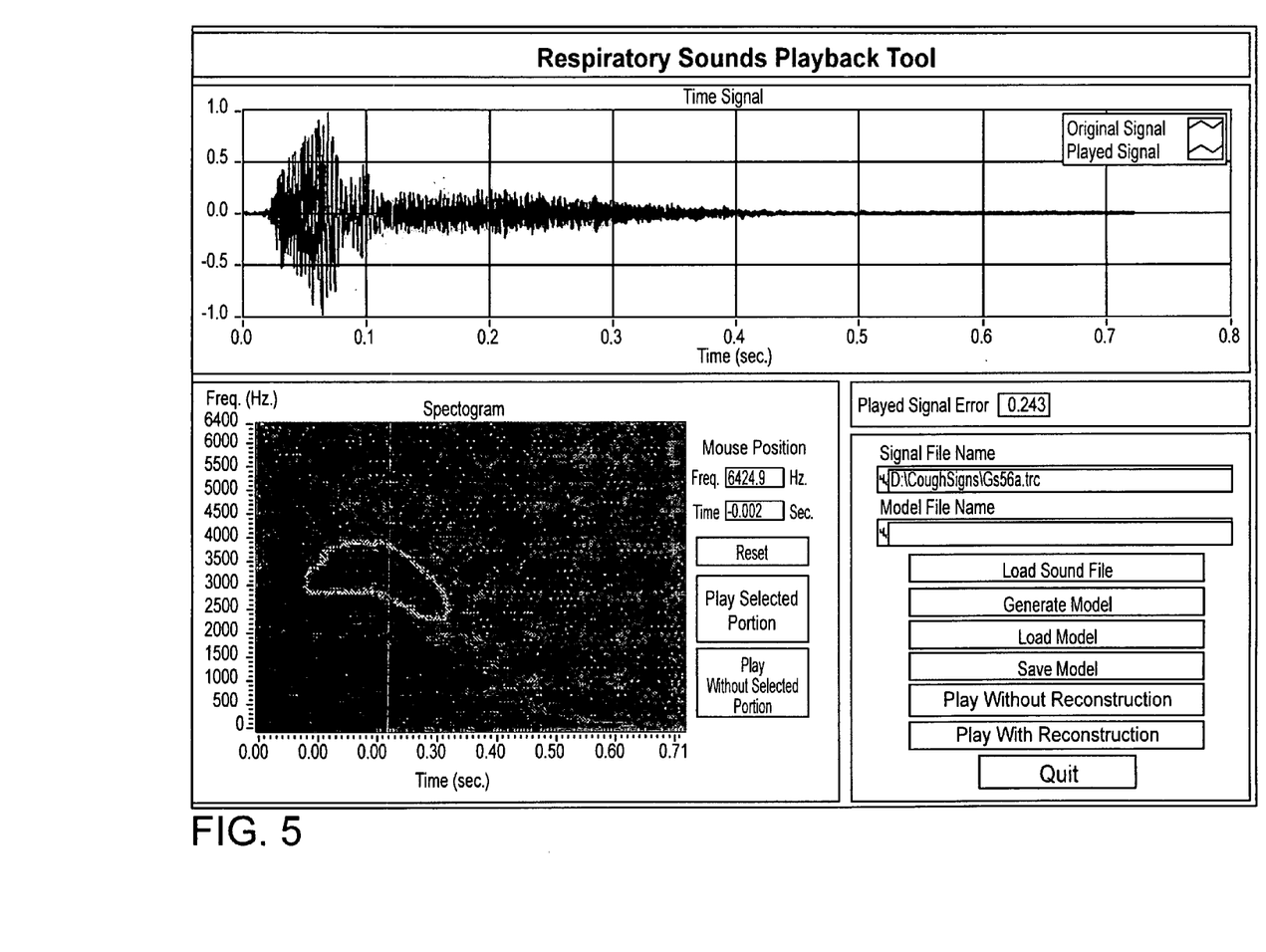
FIG. 5 shows the main user screen of a graphical user interface program.

Referring to FIG. 5, the main user screen of the program is shown. The panel on the lower right hand side of the main user screen includes buttons for performing various functions. For example, depressing the "Load Sound File" button allows a user to select a sound file from a database of pre-recorded sounds. As shown, the currently loaded sound file is displayed in a text field in the lower right hand panel. The selected sound file, which in the illustrated example is a sound file for a cough, can be played without reconstruction by selecting the "Play Without Reconstruction" button.

To play the sound file using the reconstruction technique described herein, an inverse model of the playback system is needed. To obtain an inverse model, a user can either generate a new model or load a previously generated model. Depressing the "Generate Model" button will play the currently loaded sound file and use the output from the playback system to generate a new inverse model. Once generated, a new model can be saved for later use by entering a file name for the model in the "Model File Name" text field and depressing the "Save Model" button. Alternatively, depressing the "Load Model" button allows a user to select a previously generated model, which may comprise, for example, a model previously generated with the same sound file, a different sound file or a white noise file. The file name of the selected model will be displayed in the "Model File Name" text field. In any case, after a playback system model is obtained, the sound can be played with reconstruction by depressing the "Play With Reconstruction" button. A "Quit" is provided to allow a user to exit the program.

When a sound file is played (with or without reconstruction), a time signal display on the top half of the main user screen displays the time signal of the original signal (i.e., the signal of the originally recorded sound) and the time signal of the played signal in contrasting colors. As shown, the peak magnitudes of the signals are normalized to 1.0 to compensate for amplitude differences caused by the amplifier gain. A text display below the time signal display shows the average amplitude error between these two signals.

As further shown in FIG. 5, a spectrogram of the selected sound file is displayed in the lower left panel of the main user screen. The spectrogram in the form shown comprises a horizontal time axis and a vertical frequency axis. Energy distribution is represented by a color scale in which different colors correspond to different bands of energy.

The program allows a user to select a specific component of the sound file for playing in the playback system. In the illustrated embodiment, for example, this is accomplished by freehand drawing a line with the mouse around a portion or region of the spectrogram corresponding to the specific sound component so as to define an enclosed portion of the spectrogram. When drawing with the mouse, the horizontal and vertical positions of the mouse in the spectrogram (i.e., the time and frequency coordinates) are displayed in separate text fields to the right of the spectrogram. In the illustrated example, the enclosed portion is shown as a narrow band of high intensity energy centered around 3200 Hz. This portion of the spectrogram represents a continuous high-pitch lung sound, referred to as a "wheeze."

Drawing mechanisms other than a conventional computer mouse may be used to draw a line around the selected portion of the spectrogram. For example, a light pen or a touch screen could be employed.

Figure 6:
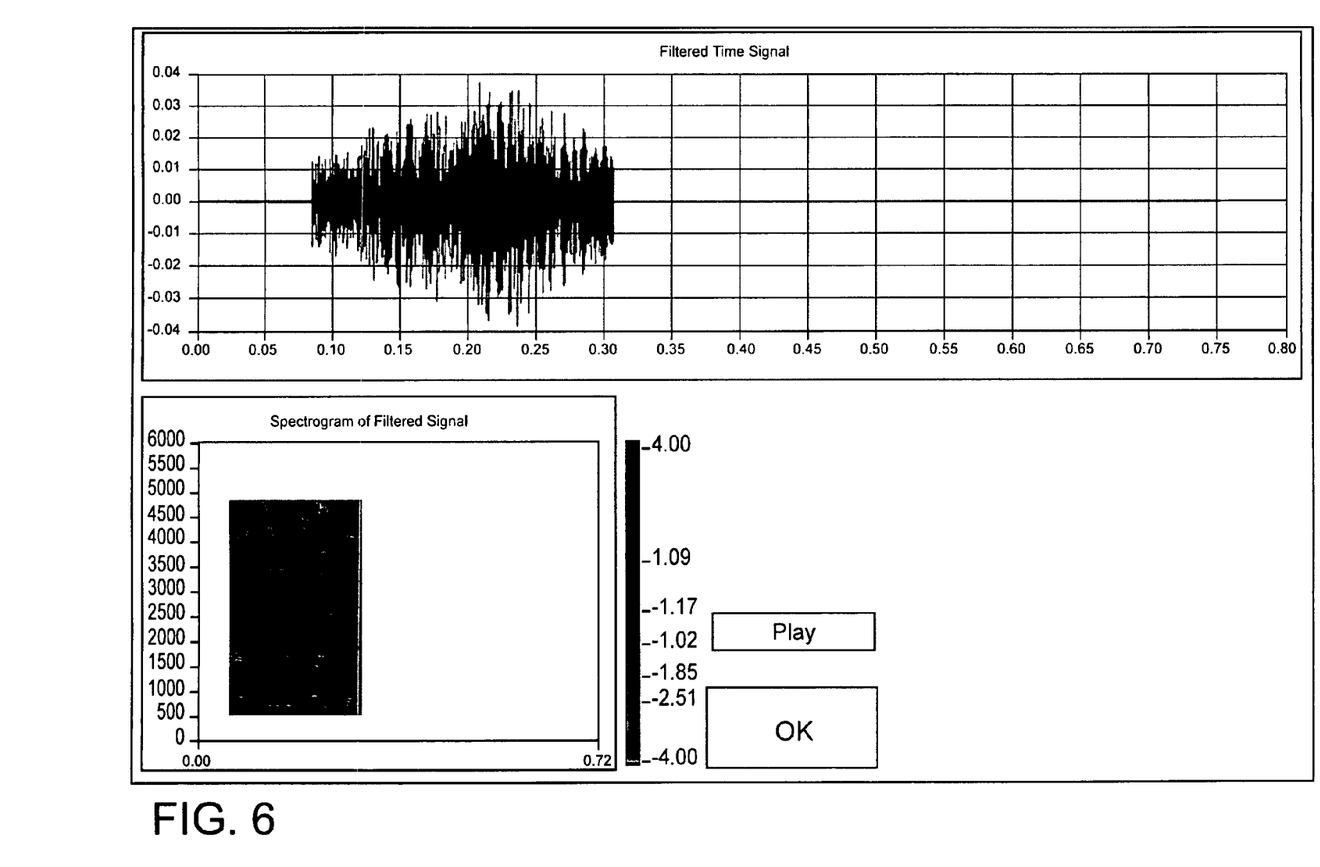
FIG. 6 shows the filtered signal screen of the graphical user interface program of FIG. 5.

When the "Play Selected Portion" button of the lower left hand panel is depressed, the enclosed portion of the spectrogram is filtered or extracted from the unwanted portion of the sound (i.e., the portion of the spectrogram surrounding the enclosed portion) and a filtered signal screen is opened as shown in FIG. 6. In a working embodiment, for example, the program uses a second order, time-varying Butterworth filter to filter the enclosed portion from the unwanted portion of the spectrogram. In addition, the filter cut-off frequencies may be changed every 20 ms based on the user selection.

The lower half of the filtered signal window shows a spectrogram of the signal after it is processed by the Butterworth filter. As shown, the selected "wheeze" remains while most other sound components have been removed by the filter. Displayed to the right of the spectrogram is a key for the color scale of the spectrogram to facilitate interpretation of the energy intensity of the selected portion. The top half of the filtered signal screen shows a time signal of the filtered signal. Depressing the "Play" button will play the selected sound component (i.e., the "wheeze") in the playback system. If an inverse system model is currently loaded, then the selected sound component is played with reconstruction. If an inverse system model is not currently loaded, then the sound component is played without reconstruction.

Referring again to FIG. 5, the program also permits playback of the sound file without the selected sound component by depressing the "Play Without Selected Portion" after an enclosed portion of the spectrogram is defined using, for example, the freehand drawing method described above. Selection of the "Play Without Selected Portion" will open a filtered signal screen similar to that shown in FIG. 6 except that the spectrogram and time signal will be that of the sound file with the selected sound component removed. A "Play" button, such as the one shown in FIG. 6, is provided to play the sound in the playback system without the selected portion of the spectrogram (e.g., the "wheeze" shown in FIG. 5).

Figure 4:
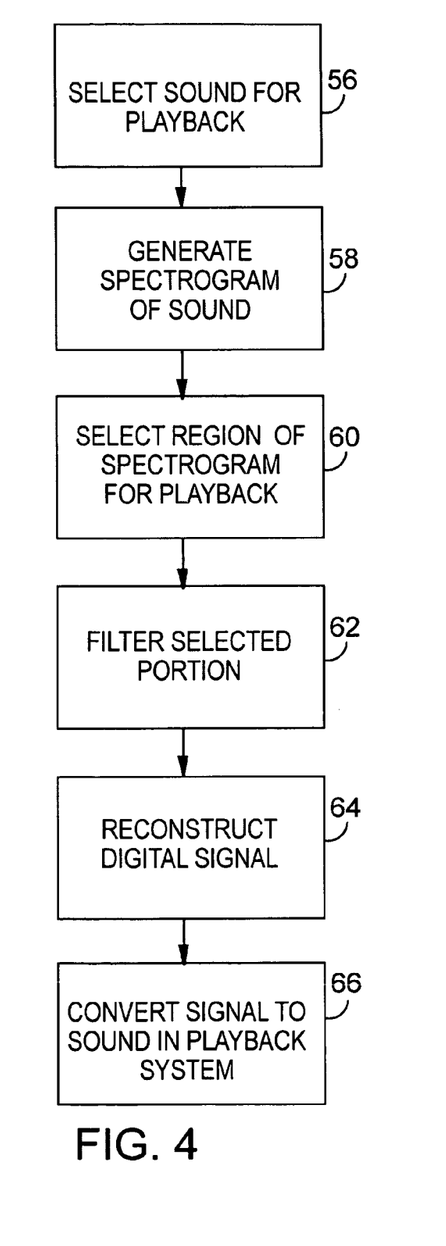
FIG. 4 is a flowchart showing a method for playing a specific component of a pre-recorded sound.

FIG. 4 shows a flowchart for a method of playing a specific component of a pre-recorded respiratory sound in a playback system. First, a pre-recorded sound is selected (process block 56) and a spectrogram of the sound is generated (process block 58). In process block 60, a portion of the spectrogram corresponding to a specific component of the sound is selected for playback using, for example, the freehand drawing technique described above. Once a portion of the spectrogram is selected, it is then filtered from the remaining portion of the spectrogram using, for example, a second order Butterworth filter, to provide a signal for the specific sound component (process block 62). In process block 64, the signal may be reconstructed using an inverse model of the playback system. Finally, the signal is converted into an audible sound in the playback system, as indicated in process block 66.

In an alternative embodiment, a database of pre-reconstructed sound signals is stored on the computer. In this case, the program allows a user to select one of the pre-reconstructed sounds for accurate playback and an inverse model is not required.

The present invention has been shown in the described embodiments for illustrative purposes only. The present invention may be subject to many modifications and changes without departing from the spirit or essential characteristics thereof. We therefore claim as our invention all such modifications as come within the spirit and scope of the following claims.

We claim:

1. An auscultatory training apparatus comprising:
   a playback system;
   a computer having memory means for digitally storing a database of pre-recorded, physiological sounds for playing on the playback system, means for selecting one of the pre-recorded sounds for playback, means for generating an input digital signal of the sound selected for playback, a digital to analog converter for converting the digital signal into an input analog signal, an analog to digital converter to receive an analog output signal from the playback system and convert the output signal to a digital signal, and reconstruction means for reconstructing the input digital signal so as to cancel the distortions of the playback system for accurate audible reconstruction of the sound in the playback system, wherein the reconstruction means comprises an inverse model of the playback system in the form of a digital infinite impulse response filter; and the playback system including an amplifier for receiving and amplifying the input analog signal from the digital to analog converter, an output speaker connected to the amplifier for converting the analog signal received from the amplifier into an audible reconstruction of the selected sound, an elongate tubular member positioned proximate the speaker so that sound from the speaker travels through the tubular member, a listening mechanism operatively coupled to the tubular member to enable a user to listen to the reconstructed sound, and a microphone mounted on the tubular member and connected to the analog to digital converter, the microphone operable to convert the audible sound into an output analog signal and transmit the output signal to the analog to digital converter.

2. The apparatus of claim 1 further comprising display means for displaying a time signal of the selected sound and a time signal of the reconstructed sound to provide a visual indication of the fidelity of the reconstructed sound.

3. The apparatus of claim 1 further comprising means for selecting a specific sound component of the selected pre-recorded sound for playing in the playback system.

4. The apparatus of claim 3 further comprising display means for displaying a spectrogram of the sound selected for playback, means for selecting a region of the spectrogram corresponding to a specific component of the sound, and means for filtering the selected component from the sound so that only the selected component of the sound is audible during playback.

5. The apparatus of claim 1 wherein the listening mechanism comprises a stethoscope comprising a pair of earpieces and a tube acoustically coupled to the earpieces and having an input end disposed inside the tubular member at a location adjacent the microphone so that the microphone and the input end of the stethoscope obtain approximately the same sound pressure wave.

6. The apparatus of claim 5, wherein the speaker is located at one end of the tubular member spaced from the microphone and the input end of the stethoscope.

7. An auscultatory training apparatus comprising:

a playback system:

memory means for digitally storing a database of pre-recorded, physiological sounds for playing on the playback system;

means for selecting one of the pre-recorded sounds for playback;

display means for displaying a spectrogram of the sound selected for playback;

means for selecting a region of the spectrogram corresponding to a specific component of the sound;

means for filtering the selected component from the sound so that only the selected component of the sound is audible during playback; and reconstruction means for reconstructing the selected sound component so as to cancel the distortions of the playback system for accurate audible reconstruction of the sound component in the playback system;

wherein the playback system comprises an output speaker for producing an audible form of the selected sound component, an elongate tubular member coupled to the speaker so that sound from the speaker travels through the tubular member, and a listening mechanism operatively coupled to the tubular member to enable a user to listen to the reconstructed sound component.

8. The apparatus of claim 7 wherein the reconstruction means comprises an inverse model of the playback system in the form of a digital infinite impulse response filter.

9. The apparatus of claim 7, wherein the speaker is located at one end of the tubular member and the listening mechanism comprises a stethoscope having an end portion disposed in the tubular member at a location spaced from the speaker.

* * * * *

UNITED STATES PATENT AND TRADEMARK OFFICE
CERTIFICATE OF CORRECTION

PATENT NO. : 7,209,796 B2  Page 1 of 1
APPLICATION NO. : 10/135964
DATED : April 24, 2007
INVENTOR(S) : McKinney et al.

It is certified that error appears in the above-identified patent and that said Letters Patent is hereby corrected as shown below:

In the Specification:

Column 5, Lines 39-41, the formula:

$$1/H(z) = \frac{1 + a_1 z^1 + a_2 z^2 + \ldots a_{100} z^{100}}{b_0 + b_1 z^1 + b_2 z^2 + \ldots b_{100} z^{100}}$$

Should read:

$$1/H(z) = \frac{1 + a_1 z^{-1} + a_2 z^{-2} + \ldots a_{100} z^{-100}}{b_0 + b_1 z^{-1} + b_2 z^{-2} + \ldots b_{100} z^{-100}}$$

Signed and Sealed this

Twenty-second Day of July, 2008

JON W. DUDAS
*Director of the United States Patent and Trademark Office*